United States Patent [19]

Preiss et al.

[11] 4,294,827
[45] Oct. 13, 1981

[54] ANTIBACTERIAL AND GROWTH PROMOTING β-LACTAM ANTIBIOTICS CARRYING AN -YLIDENE-2-PYRROLIDINON-1-YL RADICAL

[75] Inventors: Michael Preiss; Karl G. Metzger, both of Wuppertal, Fed. Rep. of Germany

[73] Assignee: Bayer Aktiengesellschaft, Leverkusen, Fed. Rep. of Germany

[21] Appl. No.: 862,452

[22] Filed: Dec. 20, 1977

[30] Foreign Application Priority Data

Dec. 24, 1976 [DE] Fed. Rep. of Germany ....... 2658905

[51] Int. Cl.³ ................. A61K 31/655; C07D 499/68; C07D 501/22; C07D 501/34
[52] U.S. Cl. ................................ 424/226; 260/239.1; 424/246; 424/263; 424/267; 424/271; 544/21; 544/22; 544/25; 544/27; 544/28
[58] Field of Search ..................... 260/239.1; 224/271; 424/246, 226, 263, 267; 544/21, 22, 25, 27, 28

[56] References Cited

FOREIGN PATENT DOCUMENTS

| | | | |
|---|---|---|---|
| 2025414 | 12/1971 | Fed. Rep. of Germany | ... 260/239.1 |
| 2025415 | 12/1971 | Fed. Rep. of Germany | ... 260/239.1 |
| 2152968 | 4/1973 | Fed. Rep. of Germany | ... 260/239.1 |
| 2151967 | 5/1973 | Fed. Rep. of Germany | ... 260/239.1 |

*Primary Examiner*—Robert Gerstl
*Assistant Examiner*—Vera C. Clarke
*Attorney, Agent, or Firm*—Sprung, Felfe, Horn, Lynch & Kramer

[57] ABSTRACT

New β-lactam antibiotics carrying a terminal -ylidene-2-pyrrolidinon-1-yl radical and of the formula

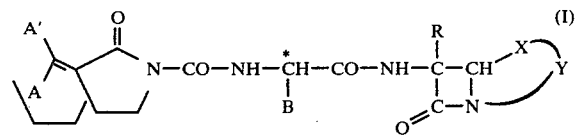

in which
  A and A' represent hydrogen, optionally substituted alkyl, aryl or a group of the formula $R_1$—X'
in which
  X' denotes a —CO— or —$SO_2$— group and
  $R_1$ denotes hydrogen, optionally substituted alkyl, aryl, thienyl, furyl, amino, monoalkylamino, dialkylamino, pyrrolidyl or piperidyl, it being furthermore possible for $R_1$ to denote alkoxy if X' represents the —CO— group;
R represents H or $OCH_3$
B represents phenyl, methylphenyl, chlorophenyl, hydroxyphenyl, furyl or the radical

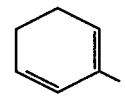

X represents S, O, SO, $SO_2$ or —$CH_2$—; and
Y represents the group

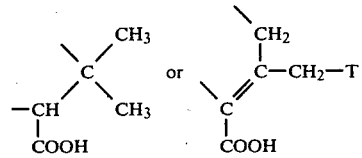

in which
the carbon atom which carries the carboxyl group is bonded to the nitrogen atom of the β-lactam ring and T denotes hydrogen, alkyl-CO-O, pyridinium, amino-pyridinium, carbamoyloxy, azido, cyano, hydroxyl, the group -S-phenyl, which can be substituted, or the group —S—Het,
in which
Het represents an optionally substituted heterocyclic 5-membered or 6-membered ring;
or a salt thereof, exhibit antibacterial and animal growth promoting activity.

17 Claims, No Drawings

ANTIBACTERIAL AND GROWTH PROMOTING β-LACTAM ANTIBIOTICS CARRYING AN -YLIDENE-2-PYRROLIDINON-1-YL RADICAL

The present invention relates to new β-lactam antibiotics, a process for their preparation and their use as medicaments, especially as antibacterial agents and as agents for promoting growth and improving the feedstuff utilisation in animals.

It has already been disclosed that certain α-(imidazolidin-2-oxo-1-yl-carbonylamino)-benzylpencillins have an antibacterial action [compare German Offenlegungsschriften (German Published Specifications) Nos. 2,152,968, 2,152,967, 2,025,414 and 2,025,415].

The present invention provides β-lactam antibiotics of the formula (I)

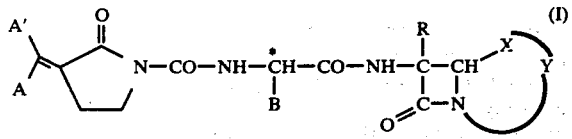

in which
A and A' represent hydrogen, optionally substituted alkyl, aryl or a group of the formula $R_1$—X',
in which
X' denotes —CO— or —SO$_2$— and
$R_1$ denotes hydrogen, optionally substituted alkyl, aryl, thienyl, furyl, amino, monoalkylamino, dialkylamino, pyrrolidyl or piperidyl, it being furthermore possible for $R_1$ to denote alkoxy if X' represents the —CO group;
R represents H or —OCH$_3$
B represents phenyl, methylphenyl, chlorophenyl, hydroxyphenyl, furyl or the radical

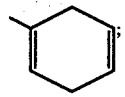

X represents the group S, SO, SO$_2$, or —CH$_2$—; and
Y represents the group

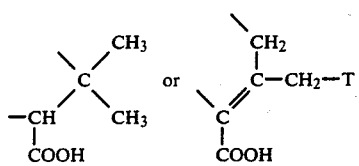

in which
the carbon atom which carries the carboxyl group is bonded to the nitrogen atom of the β-lactam ring and T denotes hydrogen, alkyl-CO—O—, pyridinium, aminopyridinium, carbamoyloxy, azido, cyano, hydroxyl, the group —S-phenyl, which can be substituted, or the group —S-Het,
in which
Het represents an optionally substituted heterocyclic 5-membered or 6-membered ring;
and which can be in either one of the two possible configurations, that is the R- and S-configurations, with respect of the chirality centre C*, or a mixture of the diastereomers resulting therefrom, and their salts.

Above all, the new β-lactam antibiotics according to the invention differ chemically from the known compounds of the state of the art in that a nitrogen atom of the imidazolidinone radical is replaced by a ylidene grouping.

The compounds of the invention (i.e. the compounds of the formula (I) and their salts) have strong antibacterial properties and possess the property of improving growth and feedstuff utilisation in animals. Consequently, of those compounds of the invention which are salts, the pharmaceutically acceptable salts are most important.

Furthermore, it has been found that the compounds of the invention are obtained when compounds of the formula (II)

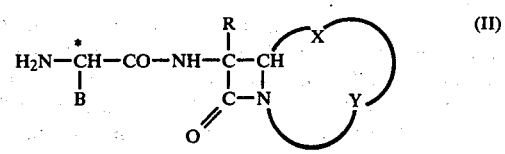

are reacted with compounds of the formula (III)

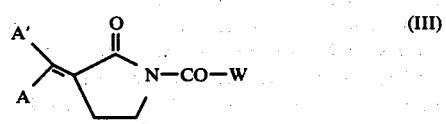

in which
A and A' have the meaning indicated above and
W represents halogen, azide or another nucleofugic leaving group,
in the presence of a solvent and, optionally, of an acid-binding agent at temperatures from −20° C. to +50° C. and the resulting β-lactam antibiotics are optionally converted into their non-toxic, pharmaceutically acceptable salts, or, if desired, the free acids are prepared from the salts which are obtained.

Surprisingly, the compounds according to the invention show, coupled with good tolerance, a considerably higher and, above all, broader antibacterial action, that is to say action against several bacteria families in the Gram negative range, than, for example, the β-lactam antibiotics known from the state of the art.

If, for example, D-α-aminobenzylpenicillin and 1-chlorocarbonyl-3-benzylidene-2-pyrrolidinone are used as the starting materials, the course of the reaction can be represented by the following equation:

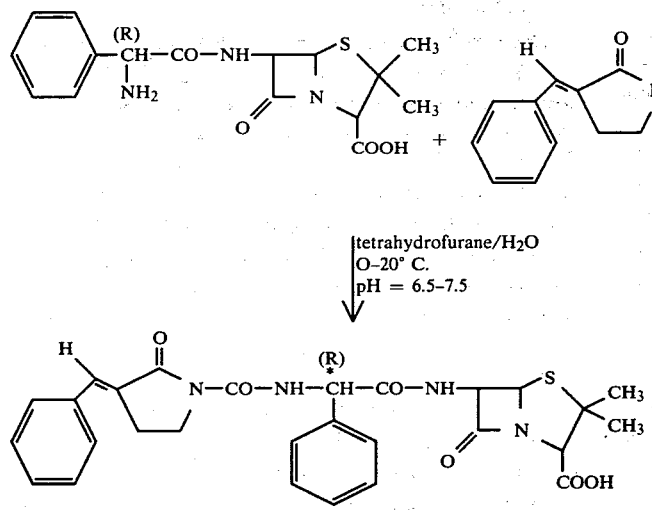

|tetrahydrofurane/H₂O
|0–20° C.
|pH = 6.5–7.5

In the general formulae, preferred optionally substituted alkyl groups for the radicals A, A' and R₁ are straight-chain or branched alkyl groups with 1 to 4, in particular 1 or 2, carbon atoms.

Examples which may be mentioned are optionally substituted methyl, ethyl, n- and i-propyl and n-, i- and t-butyl.

The alkyl groups in the radicals A, A' and R₁ can carry one or more, preferably 1 to 5, in particular 1 to 3, identical or different substituents. Examples of substituents which may be mentioned are: halogen, preferably fluorine, chlorine, bromine and iodine, especially fluorine, chlorine and bromine; cyano and nitro. Examples of substituted alkyl groups in the radicals A, A' and R₁ which may be mentioned are: chloromethyl, fluoromethyl, trifluoromethyl, chlorodifluoromethyl, β,β,β-trifluoroethyl, pentafluoroethyl, cyanomethyl, β-cyanoethyl, γ-cyanopropyl, nitromethyl, β-nitroethyl and γ-nitropropyl. When R₁ represents an alkyl group it can furthermore carry a R₂-SO group, R₂ representing straight-chain or branched alkyl with 1 to 4, in particular 1 or 2, carbon atoms, such as methyl, ethyl, n- and i-propyl and n-, i- and t-butyl. Preferred substituted alkyl groups for the radicals A and A' are methyl, ethyl, cyanomethyl and β-cyanoethyl and preferred optionally substituted alkyl groups for the radical R₁ are methyl, ethyl, cyanomethyl, cyanoethyl, trifluoromethyl, pentafluoroethyl and methylsulphonylmethyl.

Suitable aryl radicals for the radicals A, A' and R₁ are phenyl or naphthyl, preferably phenyl or furyl.

The preferred monoalkylamino and dialkylamino radicals for the radical R₁ contain 1 to 4, in particular 1 or 2, carbon atoms per alkyl group. Examples which may be mentioned are: methylamino, diethylamino, dimethylamino and methylethylamino. Methylamino, ethylamino and dimethylamino are preferred.

When R₁ represents pyrrolidyl or piperidyl the groups are preferably bonded to X' via their nitrogen atoms.

If X' represents the CO group, R₁ can also denote alkoxy. Preferred alkoxy groups for R₁ are straight-chain or branched alkoxy groups with 1 to 4, in particular 1 or 2, carbon atoms. Examples which may be mentioned are methoxy, ethoxy, n- and i-propoxy and n-, i- and t-butoxy. Methoxy is preferred.

When R₁ represents thienyl or furyl the groups are preferably bonded in their 2-positions.

When B represents methylphenyl, chlorophenyl or hydroxyphenyl, the methyl, chlorine and hydroxy groups can be in the ortho-position, para-position or meta-position relative to the bond on the phenyl ring. The para-position is preferred.

In the definition of T, alkyl in alkyl—CO—O— preferably denotes alkyl with 1 to 4, in particular 1 or 2, carbon atoms. Examples which may be mentioned are methyl and ethyl, methyl being particularly preferred.

The heterocyclic ring Het in —S-Het in the definition of T consists of 5 or 6 ring members and contains 1 to 4, preferably 1 to 3, identical or different hetero-atoms, hetero-atoms being oxygen, sulphur and nitrogen. The heterocyclic ring is preferably unsaturated and particularly preferably contains 2 double bonds. The heterocyclic ring can contain one or more, preferably 1 or 2, in particular 1, substituent. Examples of substituents which may be mentioned are: halogen, such as fluorine, chlorine, bromine and iodine, preferably chlorine and bromine, amino, lower alkylamino, di-lower alkylamino, lower alkyl, cycloalkyl (with 3 to 7, preferably 5 or 6, carbon atoms in the cycloalkyl part), lower alkoxy (for the meaning of "lower alkyl" see above), trifluoromethyl, phenyl, benzyl and acylamino with preferably 2 to 5, in particular 2 or 3, carbon atoms. The following radicals may be mentioned as particularly preferred for -S-Het:

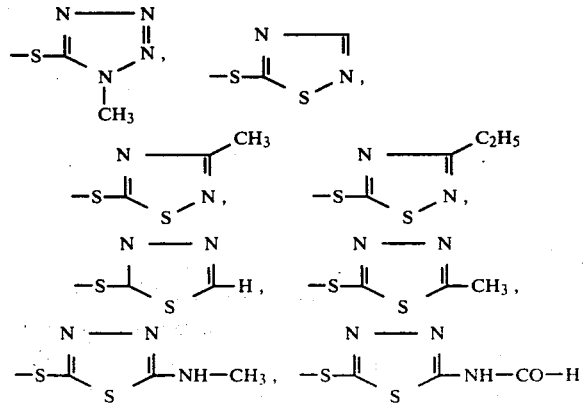

-continued

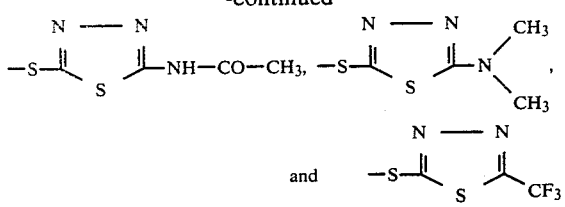

and 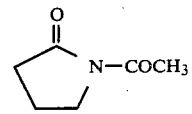

The —S-phenyl radical in the definition of T can carry one or more, preferably 1 to 3, in particular 1 or 2, identical or different substituents, preferred substituents being those which are listed above as possible substituents of the radical —S—Het.

Compounds according to the invention in which C* is present in the D—=R-configuration are very particularly preferred.

All crystal forms and hydrate forms of the compounds of the general formula I according to the invention and their salts are antibacterially active in the same way and are included within the present invention.

When W is a halogen atom, it usually represents fluorine, chlorine, or bromine, preferably bromine or chlorine, especially chlorine.

The radical W may also represent any of the nucleofugic groups customarily used in organic chemistry, and above all those which are described in Angewandte Chemie, 81 (1969), page 543.

The compounds of the formula I from salts with inorganic and organic bases at the acid carboxyl group or respectively, at the acid carboxyl and sulphonic acid groups. Any of the bases customarily used in pharmaceutically chemistry, especially in the chemistry of antibiotics, can be employed to form the salts. Examples of inorganic bases which may be mentioned are: alkali metal hydroxides and alkaline earth metal hydroxides, alkali metal carbonates and alkaline earth metal carbonates and alkali metal bicarbonates, such as sodium hydroxide and potassium hydroxide, calcium hydroxide and magnesium hydroxide, sodium carbonate and potassium carbonate, calcium carbonate and sodium bicarbonate and potassium bicarbonate; aluminium hydroxide and ammonium hydroxide. Organic amines which can be employed are primary, secondary and tertiary aliphatic amines as well as heterocyclic amines. Examples which may be mentioned are: di- and tri-lower alkylamines, for example diethylamine and triethylamine, tri-β-hydroxyethylamine, procaine, dibenzylamine, N,N'-dibenzylethylenediamine, N-benzyl-β-phenylethylamine, N-methyl- and N-ethyl-morpholine, 1-ephenamine, dehydroabietylamine, N,N'-bis-dehydroabietylethylenediamine and N-lower alkylpiperidine. So-called basic aminoacids, such as lysine or arginine, can also advantageously be used as bases. Particularly preferred salts are the sodium salts.

The compounds of the general formula II used as starting materials are already known or can be obtained in accordance with known methods.

All crystal forms, hydrate forms and salts of the compounds of the general formula II are suitable starting mafterials for the process according to the invention.

Examples which may be mentioned are: α-aminobenzylpenicillin, α-amino-p-hydroxybenzylpenicillin, α-amino-p-methyl-benzylpenicillin, α-amino-p-chlorobenzylpenicillin, 6-[2-amino-2-(1,4-cyclohexadien-1-yl)-acetamido]-penicillanic acid, 7-(α-amino-phenylacetamido)-3-methyl-ceph-3-em-4-carboxylic acid, 7-(α-amino-phenylacetamido)-3-acetoxymethyl-ceph-3-em-4-carboxylic acid and 7-(α-amino-4-hydroxy-phenylacetamido)-3-acetoxymethyl-ceph-3-em-4-carboxylic acid.

The compounds of the general formula (III) used as starting materials can be obtained in accordance with known methods. For example, they can be obtained by the following route [compare J. Heterocycl. Chem. 2, 171 (1965)]:

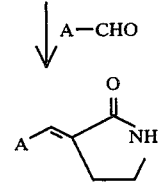

↓ A—CHO

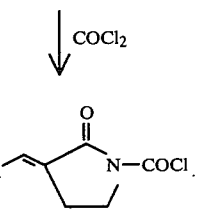

↓ COCl$_2$

Examples which may be mentioned of the starting compounds, according to the invention, of the general formula (III) are: 3-benzylidene-1-chlorocarbonyl-2-pyrrolidinone, 3-(4-chlorobenzylidene)-1-chlorocarbonyl-2-pyrrolidinone, 3-furfurylidene-1-chlorocarbonyl-2-pyrrolidinone, 3-(5-methylfurfurylidene)-1-chlorocarbonyl-2-pyrrolidinone, 3-ethylidene-1-chlorocarbonyl-2-pyrrolidinone and 3-isopropylidene-1-chlorocarbonyl-2-pyrrolidinone.

Those compounds of the general formula II in which W is azide are obtained in the customary manner, for example from the corresponding compounds II in which W is halogen, by reaction for example, with alkali metal azides.

Diluents which can be used in the process according to the invention include water and all the inert organic solvents, preferably those which are water-miscible. These include, above all, lower dialkyl ketones, for example acetone and methyl ethyl ketone, and cyclic ethers, for example tetrahydrofurane and dioxane; nitriles, for example acetonitrile; lower dialkylformamides, for example dimethylformamide; lower alkyl alcohols, for example ethanol and isopropanol, and dimethylsulphoxide. These solvents can also be used in mixtures with one another and in any desired mixtures of one or more of these solvents with water. The process according to the invention can thus be carried out in the presence of: (a) exclusively water, (b) exclusively one or more organic solvents or (c) water and one or more organic solvents. If, because of the presence of water, it is possible to measure the pH during the reaction according to the invention, the pH of the reaction mixture is preferably kept between 6.5 and 7.5 by adding bases or by using buffer mixtures. However, the process according to the invention can also be very well carried out in another pH range, for example between 4.5 and 9.0 or at pH 2.0 to 4.5. Furthermore, it is possible to carry out the reaction in solvents which are not water-miscible, for example halogenated hydrocarbons, such as chloroform or methylene chloride, with the addition of organic bases, preferably lower alkylamines, for example triethylamine or diethylamine, or cyclic bases, for example N-ethylpiperidine. Moreover, the reaction can be carried out in a mixture of water and a solvent which is not water-miscible, such as, for example, lower alkyl ethers, such as diethyl ether, and halogenated hydrocarbons, such as chloroform and methylene chloride; carbon disulphide; isobutyl methyl ketone; esters, such as ethyl acetate; and aromatic hydrocarbons, such as benzene, it being appropriate to stir the mixture vigorously and to keep the pH value between 4.5 and 9.0 or, for example, 2.0 and 4.5 by adding bases or using customary buffer solutions, for example phosphate buffers, acetate buffers or citrate buffers. However, the reaction can also be carried out alone in water in the absence of organic solvents in the presence of an organic or inorganic base or with the addition of customary buffer substances.

All the acid-binding agents customarily used in the chemistry of antibiotics can be used as the acid-binding agent. These include inorganic bases and organic bases which, for example because of steric hindrance, are difficult to acylate. Examples of inorganic bases which may be mentioned are sodium hydroxide and potassium hydroxide. Virtually all the open-chain or cyclic amines which cannot be acylated or which are difficult to acylate and also heteroaromatic bases can be used as organic bases. Examples of bases which may be mentioned are tertiary amines, preferably lower alkylamines, for example triethylamine, and/or cyclic bases, for example pyridine, and an example which may be mentioned of a secondary amine which is difficult to acylate is dicyclohexylamine.

In the process according to the invention it is only necessary to add a base when acid compounds are formed during the reaction, for example in the case where W represents halogen or azide.

The reaction temperatures can be varied within a relatively wide range. In general, the reaction is carried out between −20° C. and +50° C., preferably between 0° and +20° C. However, as in most chemical reactions, higher or lower temperatures can in principle also be used.

The reaction can be carried out under normal pressure, but also under reduced pressure or increased pressure. In general, the reaction is carried out under normal pressure.

In carrying out the processes according to the invention, the proportion of reactants of the formulae II and III can be varied within wide limits without the result being adversely influenced. For example, the starting materials can be reacted with one another in equimolar amounts. However, it can be appropriate to use one of the two reactants in excess in order to facilitate the purification of the desired penicillin or its preparation in the pure state and to increase the yield.

For example, it is possible to employ the reactant of the general formula II in an excess of 0.1 to 0.3 molar equivalents and thereby to achieve a lower decomposition of the reactants of the general formula III in a water-containing solvent mixture. Because of their good solubility in aqueous mineral acids, the excess of the reactants of the general formula II can be easily removed during the working up of the reaction mixture.

On the other hand, however, the reactants of the general formula III can also advantageously be employed in an excess of, for example, 0.1 to 1.0 molar equivalents. The reactants of the general formula II are thereby better utilised and the decomposition of the reactants of the general formula III, which proceeds as a side-reaction in water-containing solvents, is compensated. Since the compounds of the general formula III added in excess are rapidly converted in water into neutral nitrogen-containing heterocyclic compounds which can be easily removed, the purity of the antibiotics is scarcely impaired by this procedure.

The amount of the bases, which are optionally used, is determined, for example, by the desire to maintain a particular pH value. Where a pH measurement and adjustment is not carried out or, because of the lack of sufficient amounts of water in the diluent, is not possible or is not appropriate, 2 molar equivalents of base are preferably added.

Working up of the reaction mixtures in order to prepare the compounds according to the invention, and their salts, is throughout carried out in the manner which is generally known for these substances. The isolation and purification of the compounds according to the invention and the liberation of the free acids from salts or the conversion of the free acids into salts are also carried out in accordance with methods of organic chemistry which are generally customary and which are familiar to all those skilled in the art.

Both the crystalline and the amorphous forms and both the anhydrous and the various hydrate forms of the compounds of the general formula I, in the form of the free acid, are antibacterially active in the same way. Likewise, both the crystalline and the amorphous forms and both the anhydrous and the water-containing, for example hydrate, forms of the compounds of the general formula I in the form of their salts, for example sodium salts, are antibacterially active in the same way.

The following compounds may be mentioned as new active compounds (formulae IV and V):

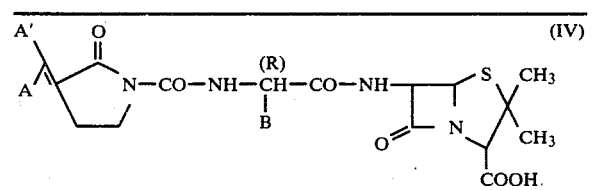

| A, A' | B |
|---|---|
| CH₃—, H— |  |
| CH₃—, CH₃— | " |
| C₆H₅, H— | " |
| p-Cl—C₆H₄—, H— | " |
| 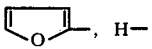, H— | " |
| CH₃—, H— | |
| CH₃—, H— | 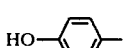 |
| 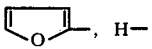, H— | 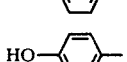 |

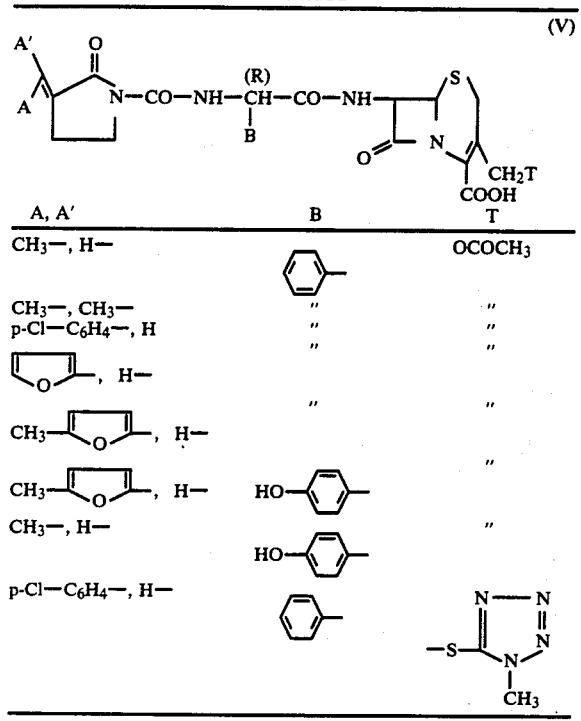

The active compounds according to the invention have a powerful and broad antimicrobial action, coupled with low toxicity. These properties enable them to be used as chemotherapeutic active compounds in medicine and as substances for preserving inorganic and organic materials, especially organic materials of all kinds, for example polymers, lubricants, paints, fibres, leather, paper and timber and foodstuffs, and water.

The active compounds according to the invention are active against a very broad spectrum of micro-organisms. With their aid it is possible to combat Gram-negative and Gram-positive bacteria and bacteria-like microorganisms and to prevent, alleviate and/or cure diseases caused by these pathogens.

The active compounds according to the invention are particularly active against bacteria and bacteria-like microorganisms. They are therefore particularly suitable for the prophylaxis and chemotherapy, in human medicine and veterinary medicine, of local and systemic infections caused by these pathogens.

For example, local and/or systemic diseases which are caused by the following pathogens or by mixtures of the following pathogens can be treated and/or prevented:

Micrococcaceae, such as Staphylococci, for example *Staphylococcus aureus*, *Staph. epidermidis* and *Staph. aerogenes*, and *Gaffkya tetragena* (Staph. = Staphylococcus);

Lactobacteriacea, such as Streptococci, for example *Streptococcus pyogenes*, α- and β-maemolysing Streptococci, non (γ-)-haemolysing Streptococci, *Str. viridans, Str. faecalis* (Enterococci), *Str. agalactiae, Str. lactis, Str. equi, Str. anaerobis* and *Diplococcus pneumoniae* (Pneumococci) (Str. = Streptococcus);

Neisseriaceae, such as *eisseriae*, for example *Neisseria gonorrhoeae* (Gonococci), *N. meningitidis* (Meningococci), *N. catarrhalis* and *N. flava* (N. = Neisseria);

Corynebacteriaceae, such as Corynebacteria, for example *Cornyebacterium diphtheriae, C. pyogenes, C. diph-theroides, C. acnes, C. parvum, C. bovis, C. renale, C. ovis* and *C. murisepticum*;

Enterobacteriaceae, such as Escherichiae bacteria of the Coli group, Escherichia bacteria, for example *Escherichia coli*, Enterobacter bacteria, for example *E. aerogenes* and *E. cloacae*, Klebsiella bacteria, for example *K. pneumoniae, K. pneumoniae* and *K. ozaenae*, Erwiniae, for example Erwinia spec., and Serratia, for example *Serratia marcescens* (E. = Enterobacter), (K. = Klebsiella), Proteae bacteria of the Proteus group: Proteus, for example *Proteus vulgaris, Pr. morganii, Pr. rettgeri* and *Pr. mirabilis*, and Providencia, for example Providencia sp., (Pr = Proteus), and Salmonellaea: Salmonella bacteria, for example Salmonella paratyphi A and B, *S. typhi, S. enteritidis, S. cholerae suis* and *S. typhimurium* (S. = Salmonella), and Shigella bacteria, for example *Shigella dysenteriae, Sh. ambigua, Sh. flexneri, Sh. boydii* and *Sh. sonnei* (Sh. = Shigella);

Pseudomonadaceae, such as Pseudomonas bacteria, for example *Pseudomonas aeruginosa* and *Ps. pseudomallei* (Ps. = Pseudomonas), and Aeromonas bacteria, for example *Aeromonas liquefaciens* and *A. hydrophila* (A. = Aeromonas);

Spirillaceae, such as Vibrio bacteria, for example *Vibrio cholerae, V. proteus* and *V. fetus* (V. = Vibrio), and Spirillum bacteria, for example Spirillum minus;

Parvobacteriaceae or Brucellaceae, such as Pasteurella bacteria, for example *Pasteurella mulrocida, Past. pestis* (Yersinia), *Past. pseudotuberculosis* and *Past. tularensis* (Past. = Pasteurella), Brucella bacteria, for example *Brucella abortus, Br. melitensis* and *Br. suis* (Br. = Brucella), Haemophilus bacteria, for example *Haemophilus influenzae*, and Bordetella bacteria, for example *Bordetella pertussis* and *B. bronchiseptica* (B. = Bordetella);

Bacterioidacea, such as Bacteroides bacteria, for example *Bacteroides fragilis* and *B. serpens* (B. = Bacteroides). Fusiforme bacteria, for example *Fusobacterium fusiforme* and Sphaerophorus bacteria, for example *Sphaerophorus necrophorus, Sph. necroticus* and *Sph. pyrogenes* (Sph. = Sphaerophorus);

Bacillaceae, such as aerobic spore-forming Bacillaceae, for example *Bacillus anthracis, B. subtilis* and *B. cereus* (B. = Bacillus), and anaerobic spore-forming clostridia, for example *Clostridium perfringens, Cl. septicium, Cl. oedematien Cl. histolyticum, Cl. tetani* and *Cl. botulinium* (Cl. = Clostridium);

The above list of pathogens is purely illustrative and is in no way to be interpreted as restrictive.

Examples which may be mentioned of diseases which can be prevented, alleviated and/or cured by the active compounds according to the invention are: diseases of the respiratory passages and of the pharyngeal cavity; otitis; pharyngitis; pneumonia; peritonitis; pyelonephritis; cystitis; endocarditis; systemic infections; bronchitis; arthritis and local infections.

The present invention provides a pharmaceutical composition containing as active ingredient a compound of the invention in admixture with a solid or liquefied gaseous diluent, or in admixture with a liquid diluent other than a solvent of a molecular weight less than 350 except in the presence of a surface active agent.

The invention further provides a pharmaceutical composition containing as active ingredient a compound of the invention in the form of a sterile or isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or sub-multiple (down to a fortieth) of a daily dose of the compound of the invention in association with a carrier and/or enclosed within an envelope. Whether the medicament contains a daily dose or, for example, a half, a third, or a quarter of a daily dose will depend on whether the medicament is to be administered once or, for example, twice, three times or four times a day respectively.

The pharmaceutical compositions according to the invention may, for example, take the form of ointments, gels, pastes, creams, sprays (including aerosols), lotions, suspensions, solutions and emulsions of the active ingredient in aqueous or non-aqueous diluents, syrups, granulates or powders.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonate; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble or water-insoluble diluents, such as polyethylene glycols and fats (e.g. cocoa oil and high esters [e.g. $C_{14}$-alcohol with $C_{16}$-fatty acid]) or mixtures of these diluents.

The pharmaceutical compositions which are ointments, pastes, creams and gels can, for example, contain the usual diluents, e.g. animal and vegetable fats, waxes, paraffins, starch, tragacanth, cellulose derivatives, polyethylene glycols, silicones, bentonites, silicic acid, talc and zinc oxide or mixtures of these substances.

The pharmaceutical compositions which are powders and sprays can, for example, contain the usual diluents, e.g. lactose, talc, silicic acid, aluminum hydroxide, calcium silicate, and polyamide powder or mixtures of these substances. Aerosol sprays can, for example, contain the usual propellants, e.g. chlorofluorohydrocarbons.

The pharmaceutical compositions which are solutions and emulsions can, for example, contain the customary diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils [for example ground nut oil], glycerol, tetrahydrofurfuryl alcohol, polyethylene glycols and fatty acid esters of sorbitol or mixtures thereof.

For parenteral administration, the solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention preferably contain about 0.1 to 99.5, more preferably from about 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluents.

The discrete coherent portions constituting the medicament according to the invention will generally be adapted by virtue of their shape or packaging, for medical administration and may be, for example, any of the following: tablets, (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 50 mg to 100 g of active ingredient.

The production of the above-mentioned pharmaceutical compositions and medicaments is carried out by any method known in the art, for example, by mixing the active ingredient(s) wit the diluent(s) to form a pharmaceutical composition (e.g. a granulate) and then forming the composition into the medicament (e.g. tablets).

This invention further provides a method of combating (including prevention, relief and cure of) the above-mentioned diseases in human and non-human animals, which comprises administering to the animals a compound of the invention alone or in admixture with a diluent or in the form of a medicament according to the invention.

The active compounds or the pharmaceutical formulations can be administered locally, orally, parenterally, intraperitoneally and/or rectally, preferably orally or parenterally, such as intravenous or intramuscular. Preferred pharmaceutical compositions and medicaments are therefore those adapted for oral or parenteral administration.

In general, it has proved advantageous both in human medicine and in veterinary medicine to administer the active compound or compounds according to the invention in total amounts of about 5 to about 1,000, preferably 20 to 200, mg/kg of body weight every 24 hours, optionally in the form of several individual administrations, in order to achieve the desired results. An individual administration contains the active compound or compounds according to the invention, preferably in amounts of about 1 to about 250, especially 10 to 100, mg/kg of body weight. However, it can be necessary to deviate from the dosages mentioned and in particular to do so as a function of the nature and the body weight of the subject to be treated, the nature and the severity of the disease, the nature of the formulation and of the administration of the medicament, and the time or interval over which the administration takes place. Thus it can suffice in some cases to manage with less than the above-mentioned amount of active compound, while in other cases the above-mentioned amount of active compound must be exceeded. The particular optimum dosage required and the type of administration of the active compounds can easily be determined by anyone skilled in the art, on the basis of his expert knowledge.

When used as feedstuff additives, the new compounds can be administered in the customary concentrations and formulations together with the feedstuff or with feedstuff formulations or with the drinking water. By this means it is possible to prevent, alleviate and/or cure an infection by Gram-negative or Gram-positive bacteria and also to achieve promotion of growth and better utilisation of the feedstuff.

The invention therefore includes a medicated fodder comprising a compound according to the invention and a nutritious material, for example oil cake, grain (e.g. barley) fish meal, soya bean meal, exhausted sugar beet chips, silage, hay or skimmed milk.

The compounds of the invention are distinguished by powerful antibacterial actions, which have been tested in vivo and in vitro, and by oral resorbability.

The compounds according to the invention can, in order to broaden the spectrum of activity and to achieve an increase in the action, especially in the case of β-lactanase-forming bacteria, be combined with other antimicrobial active compounds. Such a combination would be, for example, that with oxacillin or dicloxacillin.

The compounds according to the invention can, in order to broaden the spectrum of activity and to achieve an increase in the action, also be combined with aminoglycoside antibiotics, such as, for example, gentamycin, canamycin, sisomycin, amicacin or tobramycin.

The activity of the compounds according to the invention can be demonstrated, by way of example, by the following in vitro and in vivo experiments:

1. In vitro experiments

The compounds of Examples 1, 2 and 3, which can be regarded as typical representatives of the compounds according to the invention, were diluted to a content of 100 μg/ml with Muller-Hinton nutrient broth. In each case, the nutrient solution contained $1 \times 10^5$ to $2 \times 10^5$ bacteria per milliliter. The small tubes containing this batch were in each case incubated for 24 hours and the degree of turbidity was then determined. Freedom from turbidity indicates action. At a dosage of 100 μg/ml, the following bacterial cultures were free from turbidity (sp. = species):

Klebsiella pneumoniae; Enterobacter aerogenes sp.; Providencia; *Serratia marcescens; E. coli BE;* Salmonella sp.; Shigella sp.; Proteus, indole-negative and indole-positive; *Pasteurella pseudotuberculosis;* Brucella sp.; *Haemophilus influenzae; Bordetella bronchiseptica; Staphylococcus aureus* 133; Neisseria catarrhalis sp.; Diplococcus pneumoniae sp.; *Streptococcus pyogenes W.;* Enterococcus sp; Lactobacillus sp.; *Corynebacterium diphtheriae gravis; Corynebacterium pyogenes M; Clostridium tetani* and Pseudomonas aeruginosa sp.

2. In vivo experiments

Table 1 which follows shows the action of 3 of the compounds according to the invention against several bacteria in an animal experiment using white mice. White mice of the $CF_1$ strain were infected intraperitoneally with the particular strain of bacteria indicated.

TABLE 1

Animal experiments with white mice
Determination of the $ED_{100}$ after 24 hours

| Germ | Dose in mg of the β-lactam antibiotic of Examples 1, 2 and 3 per kg/body weight (subcutaneously) |
|---|---|
| *Escherichia coli* C 165 | 2 × 150 |
| Klebsiella 63 | 2 × 150 |

Therapy: 2 administrations: 30 minutes and 90 minutes after infection. The $ED_{100}$ is the dose at which 100% of the infected animals still survive after 24 hours.

The process according to the invention is illustrated the following examples wherein:

The α-aminobenzylpenicillin used in the examples contains about 14% of water, but anhydrous α-aminobenzylpenicillin [compare U.S. Pat. No. 3,144,445] can also equally be used.

The 7-(α-amino-phenylacetamido)-3-acetoxymethyl-ceph-3-em-4-carboxylic acid used in the examples contains 8% of water, but anhydrous 7-(α-amino-phenylacetamido)-3-acetoxymethyl-ceph-3-em-4-carboxylic acid can also equally well be used.

The water content of the starting compounds is not important in carrying out the process according to the invention.

"Ampicillin" means that α-aminobenzylpenicillin with the D-=R-configuration in the side chain.

"Cephaloglycine" means that 7-(α-amino-phenylacetamido)-3-acetoxymethyl-ceph-3-em-4-carboxylic acid with the D-=R-configuration in the side chain.

Unless otherwise stated, the NMR spectra of the compounds according to the invention were recorded in $CD_3OD$ solution. The notations have the following meanings:
s=singlet
d=doublet
t=triplet
m=multiplet
AB=AB system
Explanation of the abbreviations used in the examples:
hrs=hours
hr=hour
THF=tetrahydrofurane
ether=diethyl ether
ethyl acetate=acetic acid ethyl ester
room temperature=about 20° C.
abs.=absolute The precentage data for the yields denote yields in % of theroy.

Experimental Section (a) Starting materials.

(1) 3-Benzylidene-2-pyrrolidinone and 3-(4-chloro)-benzylidene-2-pyrrolidinone

The preparation is carried out as described by H. Zimmer, D. C. Armbruster and L. J. Trauth in J. Heterocycl. Chem. 2, 171 (1965)

(2) 3-Furfurylidene-2-pyrrolidinone

The preparation is carried out analogously to (1). The yields are between 14 and 26%. Melting point 140°-142° C. (from ethanol).

IR (KBr): 3450, 3200, 1685 and 1650 $cm^{-1}$.

NMR ($CDCl_3$): s (broad) 8.27 (NH), s 7.50 (1H), t 7.15 (CH=), s 6.50 (2H), t 3.55 (2H) and m at about 3.1 (2H) ppm ($\delta$)

mass spectrum: m/e 163.

(3) (5-Methylfurfurylidene)-2-pyrrolidinone

The preparation is carried out analogously to (1).

Yield 46%. Melting point 180°-183° C. (from methanol).

IR (KBr): 3170, 3060, 1675 and 1630 $cm^{-1}$.

NMR ($CDCl_3$): s (broad) 7.85 (NH), t 6.83 (—CH=), d 6.42 (1H) d 6.11 (1H), t 3.43 (2H), m at about 3.0 (2H) and s 2.34 (3H) ppm ($\delta$).

(4) 3-Benzylidene-1-chlorocarbonyl-2-pyrrolidinone 2.0 g (20.5 mmols) of phosgene are added to a suspension of 3.0 g (18.6 mmols) of 3-benzylidene-2-pyrrolidinone 50 ml in abs. ethyl acetate at −20°. A solution of 3.8 g (20.5 mmols) of tri-n-butylamine in 20 ml of abs. ethyl acetate is added dropwise to this mixture at 0° to 5°. After stirring for 4 hours at room temperature, dry nitrogen is passed through the mixture for 30 minutes and the mixture is then concentrated. Water is added to the oily residue, whereupon the acid chloride precipitates in the solid form. It is filtered off and dried over $P_2O_5$ and KOH is a desiccator. 3.5 g (84.5%).

IR (paraffin oil): 1780 $cm^{-1}$ (COCl).

The acid chloride is used, without further characterisation, for the subsequent reactions.

(5) 3-(4-Chlorobenzylidene)-1-chlorocarbonyl-2-pyrrolidinone and 3-(5-methylfurfurylidene)-1-chlorocarbonyl-2-pyrrolidinone are prepared analogously to (4) and further reacted directly.

(b) Active compounds according to the invention

EXAMPLE 1 Sodium 6-{D-α-[(3-benzylidene-2-pyrrolidinon-1-yl)-carbonylamino]-phenylacetamido}-penicillanate 13.6 g (33.6 mmols) of ampicillin trihydrate, suspended in 100 ml of 80% strength aqueous tetrahydrofurane, are dissolved at 0°-5° C. by adding 4% strength sodium hydroxide solution, during which the pH value should not rise above 8.3. 5.0 g (22.4 mmols) of 3-benzylidene-1-chlorocarbonyl-2-pyrrolidinone are then added and the pH value is kept at 7.5 with 2% strength sodium hydroxide solution. When no further sodium hydroxide solution is consumed (after about 20 minutes), 100 ml of water are added. The tetrahydrofurane is stripped off and the aqueous phase is extracted with ethyl acetate and brought to pH 1.8 with 0.1 N hydrochloric acid, while cooling with an ice bath. The mixture is extracted four times with ethyl acetate and the extract is dried over magnesium sulphate and concentrated. 17.0 g of the free acid are obtained. This is dissolved in 50 ml of methanol, 30 ml of a 1 M sodium caprylate solution are added and the mixture is poured into 300 ml of ether with a methanol content of 5%, whereupon the Na salt precipitates (10.3 g, 78.5%).

IR (KBr): 1760, 1700, 1660, 1595 and 1515 $cm^{-1}$.

NMR ($CD_3OD$): m 7.4 (11H), s 5.67 (1H), AB 5.50 (2H), s 4.20 (1H), m at about 3.75 (2H), m at about 2.95 (2H), s 1.58 (3H), and s 1.51 (3H) ppm ($\delta$)

EXAMPLE 2 Sodium 7-{D-α-[(3-benzylidene-2-pyrrolidinon-1-yl)-carbonylamino]-phenylacetamido}-3-acetoxymethylceph-3-em-4-carboxylate 8.8 g (19.5 mmols) of cephaloglycine dihydrate and 3.5 g (21.7 mmols) of 3-benzylidene-1-chlorocarbonyl-2-pyrrolidinone are reacted as in Example (1). The free acid which precipitates on acidification of the mixture is filtered off, washed with water, dried over $P_2O_5$ in a desiccator, dissolved in methanol and converted to the sodium salt as in Example 1. Yield: 1.5 g (11.0%) of the Na salt.

IR (KBr): 3420, 1755, 1660 and 1600 $cm^{-1}$.

EXAMPLE 3 Sodium 6-{D-α-[(3-[4-chloro-benzylidene]-2-pyrrolidinon-1-yl)-carboxylamino]-phenylacetamido}-penicillanate 13.1 g (32.4 mmols) of ampicillin trihydrate and 5.9 g (21.9 mmols) of 3-(4-chlorobenzylidene)-1-chlorocarbonyl-2-pyrrolidinone are reacted as in Example (1). Yield: 8.0 g (60.5%).

IR (KBr): 3400, 1760, 1700, 1660 and 1600 $cm^{-1}$

NMR ($CD_3OD$): m 7.45 (4+1H), s 5.68 (1H), AB 5.50 (2H), s 4.20 (1H), m at about 3.8 (2H), m at about 3.0 (2H), s 1.60 (3H) and s 1.50 (3H) ppm ($\delta$)

EXAMPLE 4 Sodium 7-{D-α-[(3-[4-chloro]-benzylidene-2-pyrrolidinon-1-yl)-carbonylamino]-phenylacetamido}-3-acetoxymethyl-ceph-3-em-4-carboxylate 11.5 g (26.3 mmols) of cephaloglycine dihydrate and 9.6 g (26.3 mmols) of 3-(4-chlorobenzylidene)-1-chlorocarbonyl-2-pyrrolidinone are reacted as in Example 2. Yield: 3.6 g (21.0%).

IR (KBr): 3420, 3280, 1760, 1700, 1660, 1640 and 1590 $cm^{-1}$.

EXAMPLE 5 Sodium 6-{D-α-[(3)-[5-methylfurfurylidene]-2-pyrrolidinon-1-yl)-carbonylamino]-phenylacetamido}-penicillanate 9.2 g (22.8 mmols) of ampicillin trihydrate and 5.3 g (13.8 mmols) of 3-(5-methylfurfurylidene)-1-chlorocarbonyl-2-pyrrolidinone are reacted as in Example (1). Yield: 0.6 g (7.7%).

Ir (KBr): 3400, 1765, 1640 and 1560 cm$^{-1}$.

It will be appreciated that the instant specification and examples are set forth by way of illustration and not limitation, and that various modifications and changes may be made without departing from the spirit and scope of the present invention.

What is claimed is:

1. A β-lactam antibiotic of the formula (I)

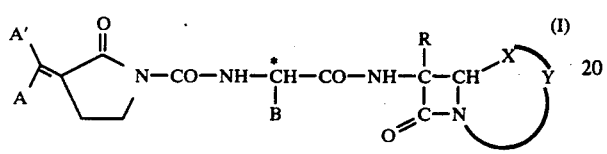

in which

A and A' represent hydrogen; alkyl of up to 5 carbon atoms optionally substituted by halogen, cyano or nitro; a phenyl, naphthyl or furyl radical; or a group of the formula $R_1$—X' in which

X' denotes a-CO— or —SO$_2$— group and $R_1$ denotes hydrogen; alkyl of up to 5 carbon atoms optionally substituted by halogen, cyano or nitro; a phenyl, naphthyl, thienyl, furyl, pyrrolidyl or piperidyl radical; amino; monoalkylamino or dialkylamino of up to 4 carbon atoms per alkyl group, it being furthermore possible for $R_1$ to denote alkoxy of up to 4 carbon atoms if X' represents the -CO-group;

R represents H or OCH$_3$,

B represents phenyl, methylphenyl, chlorophenyl, hydroxyphenyl, furyl or the radical

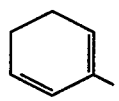

X represents S, SO or SO$_2$; and

Y represents the group

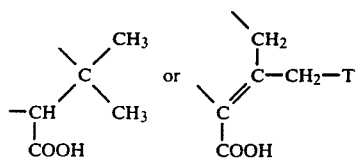

in which the carbon atom which carries the carboxyl group is bonded to the nitrogen atom of the β-lactam ring and T denotes hydrogen, C$_{1-4}$- alkyl-CO-O, pyridinium, amino-pyridinium, carbamoyloxy, azido, cyano, hydroxyl, the group -S-phenyl, which can be substituted by halogen, amino, lower alkylamino, di-lower alkylamino, lower alkyl, cycloalkyl of 3-7 ring carbon atoms, lower alkoxy, trifluoromethyl, phenyl, benzyl or acylamino with 2 to 5 carbon atoms, or the group —S—Het, in which Het represents

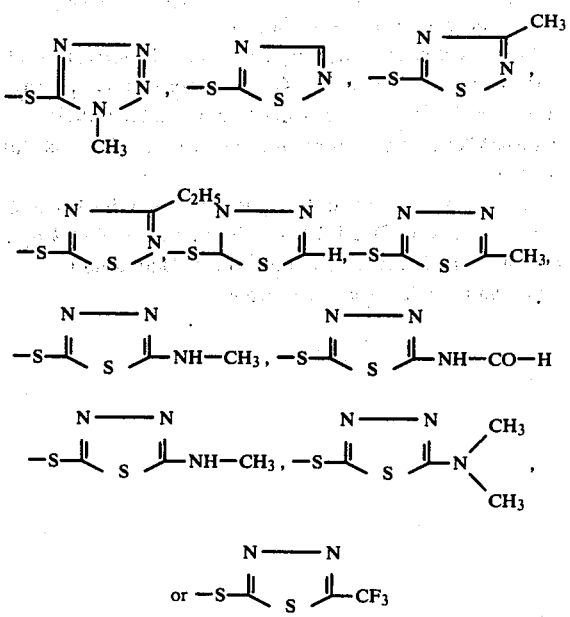

optionally substituted by halogen, amino, lower alkylamino, di-lower alkylamino, lower alkyl, cycloalkyl of 3-7 ring ring carbon atoms, lower alkoxy, trifluoromethyl, phenyl, benzyl or acylamino with 2 to 5 carbon atoms;

or a pharmaceutically acceptable salt thereof.

2. A compound according to claim 1, wherein A is a phenyl radical and A$^1$ is hydrogen.

3. A compound according to claim 1, wherein A is a furyl radical and A$^1$ is hydrogen.

4. A compound according to claim 1, wherein B is phenyl.

5. A compound according to claim 1, wherein X is S.

6. A compound according to claim 1, wherein Y is

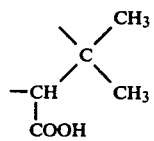

7. A compound according to claim 1, wherein Y is

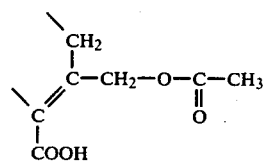

8. A compound according to claim 1, wherein such compound is 6-{D-α-[(3-benzylidene-2-pyrrolidinon-1-yl)-carbonyl-amino]-phenylacetamido}-penicillanic acid or a salt thereof.

9. A compound according to claim 1, wherein such compound is 7-{D-α-[(3-benzylidene-2-pyrrolidinon-1- yl)-carbonyl-amino]-phenylacetamido}-3-acetoxymethyl-ceph-3-em-4-carboxylic acid or a salt thereof.

10. A compound according to claim 1, wherein such compound is 6-{D-α-[(3-[4-chloro-benzylidene]-2-pyrrolidinon-1-yl)-carbonylamino]-phenylacetamido}-penicillanic acid or a salt thereof.

11. A compound according to claim 1, wherein such compound is 7-{D-α-[(3-[4-chloro-benzylidene]-2-pyrrolidinon-1-yl)-carbonylamino]-phenylacetamido}-3-acetoxymethyl-ceph-3-em-4-carboxylic acid or a salt thereof.

12. A compound according to claim 1, wherein such compound is 6-{D-α-[(3-[5-methylfurfurylidene]-2-pyrrolidinon-1-yl)-carbonylamino]-phenylacetamido}-penicillanic acid or a salt thereof.

13. An antibacterial and growth promoting composition containing as an active ingredient an effective amount of a compound according to claim 1 in admixture with a diluent.

14. An antibacterial composition in dosage unit form comprising a compound according to claim 1.

15. A method of combating bacterial diseases in human and non-human animals which comprises administering to the animals an antibacterially effective amount of a compound according to claim 1.

16. A medicament animal fodder comprising an effective amount of a compound according to claim 1 in admixture with a nutritious material.

17. A method of promoting the growth of animals which comprises feeding said animals a growth promoting amount of a compound according to claim 1.

* * * * *